US010351896B2

(12) United States Patent
Cellier et al.

(10) Patent No.: US 10,351,896 B2
(45) Date of Patent: Jul. 16, 2019

(54) **USE OF AT LEAST ONE SUBSTRATE OF CARBOXYLESTERASE AND/OR TRIACYLGLYCEROL LIPASE FOR DETECTING BACTERIA OF THE GROUP *BACILLUS CEREUS***

(71) Applicant: bioMérieux, Marcy-l'Etoile (FR)

(72) Inventors: Marie Cellier, Montalieu-Vercieu (FR); Marie-Pierre Bourguignon, Pérouges (FR); Diane Halimi, Saint Maurice de Beynost (FR)

(73) Assignee: BIOMERIEUX, Marcy-l'Etoile (FR)

( * ) Notice: Subject to any disclaimer, the term of this patent is extended or adjusted under 35 U.S.C. 154(b) by 0 days.

(21) Appl. No.: 15/107,838

(22) PCT Filed: Dec. 23, 2014

(86) PCT No.: PCT/FR2014/053547
§ 371 (c)(1),
(2) Date: Jun. 23, 2016

(87) PCT Pub. No.: WO2015/097414
PCT Pub. Date: Jul. 2, 2015

(65) Prior Publication Data
US 2016/0319326 A1 Nov. 3, 2016

(30) Foreign Application Priority Data
Dec. 24, 2013 (FR) ...................... 13 63571

(51) Int. Cl.
*C12Q 1/04* (2006.01)
*C12Q 1/44* (2006.01)

(52) U.S. Cl.
CPC ................ *C12Q 1/44* (2013.01); *C12Q 1/04* (2013.01); *G01N 2333/32* (2013.01); *G01N 2333/918* (2013.01); *G01N 2333/92* (2013.01)

(58) Field of Classification Search
CPC ....................................................... C12Q 1/04
See application file for complete search history.

(56) References Cited

U.S. PATENT DOCUMENTS

| 6,284,517 | B1 | 9/2001 | Restaino |
| 6,558,917 | B2 | 5/2003 | Schabert |
| 7,309,580 | B2 | 12/2007 | Restaino |
| 2005/0014215 | A1* | 1/2005 | Gilbert .................. C12N 1/20 |
| | | | 435/34 |

FOREIGN PATENT DOCUMENTS

| EP | 1219628 | 3/2007 |
| WO | 0138559 A2 | 5/2001 |
| WO | 2002/040706 | 5/2002 |
| WO | 2010128120 A1 | 11/2010 |
| WO | 2011033224 A1 | 3/2011 |

OTHER PUBLICATIONS

Ferencko et al., "Esterase Activity as a Novel Parameter of Spore Germination in Bacillus anthracis," Biochemical and Biophysical Research Communications, 2004, vol. 319, No. 3, pp. 854-858.
Kiernan et al., "Indigogenic Substrates for Detection and Localization of Enzymes," Biotechnic and Histochemistry, 2007, vol. 82, No. 2, pp. 73-103.
Motoyama et al., "Rapid and Sensitive Detection of Viable Bacteria in Contaminated Platelet Concentrates Using a Newly Developed Bioimaging System," Transfusion, 2008, vol. 48, No. 11, pp. 2364-2369.
Pesaresi, A., et al., "Isolation, Characterization, and Heterologous Expression of a Carboxylesterase of Pseudomonas aeruginosa PAO1", Current Microbiology, vol. 50 (2005), pp. 102-109.
Fricker et al., International Journal of Food Microbiology; 121 (2008): 27-34.
Orenga et al., 2009; J. Microbiol. Methods; 79(2):139-55.
International Preliminary Report on Patentability dated Jul. 7, 2016 for corresponding International Application No. PCT/FR2014/053547.
Kim and Goepfert, "Enumeration and Identification of Bacillus cereus in Foods: I. 24-Hour Presumptive Test Medium," Applied Microbiology, vol. 22, No. 4, (1971), pp. 581-587.
Corry et al., "Polymyxin Pyruvate Egg Yolk Mannitol Bromothymol Blue Agar (PEMBA)," Handbook of Culture Media for Food Microbiology, J.E.L. Corry et al. (Eds.), (2003), pp. 555-557.
Van Netten and Kramer, "Media for the Detection and Enumeration of Bacillus cereus in Foods: A Review," International Journal of Food Microbiology, vol. 17, (1992), pp. 85-99.

* cited by examiner

*Primary Examiner* — Rosanne Kosson
(74) *Attorney, Agent, or Firm* — Brinks Gilson & Lione

(57) ABSTRACT

Use of at least one chromogenic and/or fluorogenic carboxylesterase and/or triacylglycerol-lipase substrate, to detect bacteria of the *Bacillus cereus* group in a sample capable of containing them.

16 Claims, No Drawings

USE OF AT LEAST ONE SUBSTRATE OF CARBOXYLESTERASE AND/OR TRIACYLGLYCEROL LIPASE FOR DETECTING BACTERIA OF THE GROUP BACILLUS CEREUS*

This application is a National Stage application of International Application No. PCT/FR2014/053547 filed Dec. 23, 2014. This application also claims priority under 35 U.S.C. § 119 to FR Patent Application No. 1363571, filed Dec. 24, 2013.

BACKGROUND OF THE INVENTION

Field of the Invention

The present invention relates to the field of microbiological monitoring in the broad sense, such as microbiological monitoring of a sample of industrial or clinical origin. More particularly, the present invention deals with a method of detecting bacteria belonging to the *Bacillus cereus* group as distinct from other bacteria, by detecting hydrolysis of a carboxylesterase and/or triacylglycerol-lipase enzyme substrate.

The microbiological monitoring of samples of various origins (for example agri-food or clinical) requires the implementation of techniques which make it possible to detect microorganisms—for example for the purposes identification and/or enumeration—and of which the yield in terms of results must be as fast as possible. Generally, said microorganisms can be non-pathogenic, such as bacteria of technological interest like ferments or quality indicators; the latter make it possible to validate the production process, from raw materials to primary products, up to finished products. However, the microorganisms which are the subject of microbiological monitoring are most frequently pathogenic, which consequently necessitates their rapid and precise detection in order to start ad hoc corrective actions as soon as possible. Of course, the toxins produced by such pathogenic microorganisms—and which are wholly or partly responsible for their pathogenic character—may also be sought.

Clinical diagnosis uses the same techniques: either detection and/or enumeration of the bacteria themselves, or detection of the toxins.

In any case, and whatever the origin of the sample which is the subject of microbiological monitoring, the important factors for assessing the effectiveness of this monitoring are: the sensitivity, specificity and time-to-result.

The genus *Bacillus* includes Gram-positive bacteria ubiquitously present in nature: in the earth, water, air, in foodstuffs such as cereal grains, powdered milk, flour-based products, spices, etc. Their ability to form spores gives them a great deal of resistance in the outside environment. Spores of *Bacillus cereus* (*B. cereus*) may notably contaminate foodstuffs, from raw materials to manufactured products. The survival of said spores is guaranteed throughout the whole food chain. Under normal circumstances, *B. cereus* is present in a quantity of less than $10^3$ cells per gram of food and has no pathogenic effect. The generally permissible pathogenic level is of the order of $10^5$ cells per gram of foodstuff. The contamination of an individual from a foodstuff may therefore be responsible for gastroenteritis. Gastroenteritis linked to *B. cereus* manifests itself in either vomiting or diarrhea. Various foodstuffs may be implicated: meat, rice, dried foods, sauces, soups, etc. Opportunistic *B. cereus* infections may also be observed in vulnerable patients such as alcoholic subjects, immunosuppressed subjects, or following burn-type injuries.

The detection (for example for identification and/or enumeration purposes) of the bacteria of the *Bacillus cereus* group is therefore vital, in particular for monitoring laboratories in the agri-food industry and for those required to have clinical diagnoses carried out.

As standard, bacteria of the *Bacillus cereus* group are isolated on conventional selective culture media in dishes: for example, the standards of the ISO ("International Organization for Standardization") type or the BAM-FDA ("Bacteriological Analytical Manual of the Food and Drug Administration") methods recommend using media such as "polymyxin egg yolk mannitol bromothymol blue Agar" (which has the acronym PEMBA) or "mannitol-egg yolk-polymyxin Agar" (which has the acronym MYP). *Bacillus cereus* is identified in accordance with morphological, cultural and/or metabolic criteria. Unfortunately, these PEMBA or MYP media can give rise to false-positive results (detection specificity problem) for example due to a poor inhibiting system, or to false-negative results (sensitivity problem), for example due to the absence, in certain strains of *B. cereus*, of key morphological and/or metabolic characteristics. Finally, certain strains belonging to the *B. cereus* group exhibit ambiguous reactions, as described by Fricker et al., International Journal of Food Microbiology; 121 (2008): 27-34.

Chromogenic media in dishes have been developed in order to attempt to reduce/suppress false-negative results. Such chromogenic media contain natural or synthetic chromogenic substrates. Enzyme activities specific to certain bacterial strains are thus detected by the cleaving of these substrates. This has been described numerous times in the state of the art.

Generally, the detection specificity may be improved by adding, into the culture medium, inhibiting systems, antimicrobial and/or antifungal cocktails intended to limit the growth of the microorganisms which are not targeted/sought. However, such cocktails of inhibitors generally tend to delay the growth of the target/sought microorganisms.

Chromogenic or fluorescent media based on the detection of Phosphatidylinositol-specific phospholipase C (hereafter named PI-PLC; enzyme classification: EC 4.6.1.13), have been described in particular in U.S. Pat. No. 6,284,517, EP-B-1219628 and U.S. Pat. No. 6,558,917, as well as in the aforementioned publication by Fricker et al., 2008. Such media present, amongst others, the disadvantage of giving rise to false-negative results (detection sensitivity problem), in particular with certain strains of *Bacillus cereus, B. mycoides, B. weihenstephanensis* which do not exhibit PI-PLC activity, or a low PI-PLC activity (*B. anthracis*), or even to false-positives (detection specificity problem). Furthermore, the fluorescent substrate 4MU-MIP (4-methylumbelliferyl myo-inositol-1-phosphate) exhibits reduced stability in an aqueous medium, which imposes draconian conditions of use, in particular in terms of discontinuous measurement of fluorescence, and under precise pH conditions at that, as the aforementioned U.S. Pat. No. 6,558,917 states. More precisely, it is necessary to perform culturing at acidic pH and then alkalinise the medium to enhance the fluorescence, which is read at the end.

Description of Related Art

For its part, U.S. Pat. No. 7,309,580, describes a medium in a dish which combines a chromogenic substrate of phosphatidylcholine-specific phospholipase C (which has the acronym "PC-PLC"; enzyme classification: EC 3.1.4.3) and a chromogenic substrate of PI-PLC. The respective colours of the first substrate and of the second substrate are different and may also be distinguished from the third colour resulting from any mixing of the products of enzyme reactions of said first and second substrates.

The BCM medium, supplied by Biosynth® AG (Switzerland), uses a chromogenic substrate of PI-PLC and a system which inhibits the untargeted bacterial flora, comprising polymyxin B, trimethoprim, sulfamethoxazole and cycloheximide. The test performance is improved compared to standard media, but certain atypical strains may remain incorrectly identified (cf. Fricker et al., 2008, above).

There are chromogenic media based on the hydrolysis of β-glucosidase substrates, such as Brilliance™ *Bacillus cereus* Agar supplied by Oxoid™. However, the use of such chromogenic media generates false-positive results with the growth of certain Gram-positive bacteria expressing such an enzyme activity despite the presence of an anti-Gram positive inhibiting system comprising polymyxin B and trimethoprim, as well as false negatives (cf. Fricker et al., 2008, above).

The application PCT WO 2011/033224, in the name of the Applicant, discloses a method which is intended to make it possible to detect and/or enumerate bacteria of the *Bacillus cereus* group with the aid of a reaction medium comprising a Gram-negative bacteria inhibitor and a fluorescent phosphatidylcholine phospholipase C (PC-PLC) substrate. The PC-PLC substrate specifically described and exemplified in WO 2011/033224, namely 4 MU-CP (4-methyl-umbelliferyl-choline phosphate), is a substrate which makes it necessary to work in liquid medium and which proves to be ill-suited—or even unsuited—to detecting and/or enumerating bacteria of the *Bacillus cereus* group in agar medium. Indeed, after 4 MU-CP is cleaved by PC-PLC, the 4 MU does not remain localised in the bacterial colony belonging to the *Bacillus cereus* group but is disseminated widely within the agar medium. The fluorescence emitted is therefore not only detected around the bacterial colony belonging to the *Bacillus cereus* group but also elsewhere. In other words, the use of a fluorogenic PC-PLC substrate, such as 4 MU-CP, is ill-suited to detecting and/or enumerating bacteria of the *Bacillus cereus* group in a solid or semi-solid medium, for example in agar medium. Furthermore, from a general point of view, the fluorogenic PC-PLC substrate which is the subject of WO 2011/033224 necessitates a more or less sophisticated apparatus, such as a UV lamp, in order to detect the fluorescence induced by the cleaving of the fluorogenic substrate under the effect of the enzyme activity sought.

PCT application WO 2010/128120 (in the name of Biosynth® AG [CH]) describes Aldol®-type signalophores which consist of particular indoxyl (1H-indolyl-3-yl) derivatives, namely indoxyls joined onto the cyclic amine (N-arylated). Amongst the extremely large number of 1H-Indol-3-yl indicators tested in WO 2010/128120 for the purpose of detecting various bacterial strains, table IV c, presented on pages 79 and 80 of this document, mentions the colorimetric detection of *Bacillus cereus* strains by using a C1-Esterase Indicator, which is present at a concentration of 0.52 mM in agar medium ("Nutrient Agar"). More precisely, this C1 esterase substrate is 1-(2-Benzoylphenyl)-1H-indol-3-yl acetate.

The publication "Yasuo Motoyama et al.: "Rapid and sensitive detection of viable bacteria in contaminated platelet concentrates using a newly developed bioimaging system", TRANSFUSION, 1 Nov. 2008" discloses the use of a C1 esterase substrate, namely 5(6)-carboxyfluorescein diacetate ("CFDA"; Invitrogen, Carlsbad, Calif.) to detect several bacteria species within platelet concentrates, including *Bacillus cereus* amongst others, by detecting a fluorescence.

However, it emerges that C1 esterase substrates—such as those mentioned in WO 2010/128120 and Yasuo Motoyama et al.—are enzyme substrates with low specificity and which do not make it possible, in particular, to distinguish bacteria of the *Bacillus cereus* group from other *Bacillus* species frequently encountered, *Bacillus subtilis* in particular.

There is therefore a need to develop an application/method which is relatively simple (namely not requiring the use of a sophisticated apparatus) and which makes it possible to detect the bacteria of the *Bacillus cereus* group, in a liquid medium and in a semi-solid or solid medium, not only with very good detection sensitivity but also—and above all—with a very good detection specificity, which is sufficient to distinguish the bacteria of the *Bacillus cereus* group from other *Bacillus cereus* species frequently encountered, *Bacillus subtilis* in particular.

BRIEF SUMMARY OF THE INVENTION

In one embodiment described herein is the use of at least one chromogenic and/or fluorogenic carboxylesterase and/or triacylglycerol-lipase substrate to detect the bacteria of the *Bacillus cereus* group in a sample capable of containing them, such as a sample of agri-food origin or clinical origin, wherein said carboxylesterase and/or triacylglycerol-lipase substrate is a substrate of the general formula (I):

wherein M represents the labelling part, and
X represents an aliphatic hydrocarbon chain,
and wherein said aliphatic hydrocarbon chain comprises a number of carbon atoms between 11 and 17.

In one aspect, X represents a linear aliphatic hydrocarbon chain. In one aspect X represents a linear and saturated aliphatic hydrocarbon chain. In another aspect, the labelling part M is:
a chromogenic labelling part selected from: indoxyls, alizarin, hydroxyquinoline, catechol, dihydroxyflavone, esculetin, nitrophenol, naphthol, or at least one of their derivatives; advantageously selected from indoxyls, alizarin, hydroxyquinoline, catechol, dihydroxyflavone, esculetin, or at least one of their derivatives; or
a fluorogenic labelling part selected from: the derivatives of fluorescein, of rhodamine, of hydroxyflavone, of ELF97.

In another aspect, M represents a chromogenic labelling part, preferably selected from indoxyls, alizarin, hydroxyquinoline, catechol, dihydroxyflavone, esculetin, or at least one of their derivatives; advantageously based on indoxyl or one of its derivatives. In another aspect said aliphatic hydrocarbon chain X comprises a number of carbon atoms between 13 and 15. In another aspect, said aliphatic hydrocarbon chain X comprises 13 or 15 carbon atoms, preferably 13 carbon atoms. In another aspect, said carboxylesterase and/or triacylglycerol-lipase substrate is a substrate based on indoxyl or one of its derivatives, said carboxylesterase and/or triacylglycerol-lipase substrate being used in combination with at least an agent which promotes the oxidative polymerisation of the indoxyl derivative, such as a metal complex of the ammonium ferric citrate type. In another aspect, said carboxylesterase and/or triacylglycerol-lipase substrate is contained in a reaction medium comprising at least one, preferably two and advantageously three of the following components:
- a bacterial culture medium suitable for the bacteria to be detected, preferably a solid or semi-solid medium such as an agar medium.
- an anti-Gram negative selective system,
- an antifungal agent.

In one embodiment described herein is a method for detecting bacteria of the *Bacillus cereus* group in a solid or semi-solid medium such as an agar medium, said method comprising the following steps:
- a) placing a sample capable of containing bacteria of the *Bacillus cereus* group in contact, within said solid or semi-solid medium, with a reaction medium comprising at least one carboxylesterase and/or triacylglycerol-lipase substrate such as defined in one of claims 1 to 8 and a Gram-negative bacteria inhibitor;
- b) incubating the assembly for a time period sufficient to enable the appearance of bacterial colonies of the *Bacillus cereus* group;
- c) detecting the bacteria of the *Bacillus cereus* group through observing a coloration and/or a fluorescence caused by the hydrolysis of the carboxylesterase and/or triacylglycerol-lipase substrate by said bacteria.

In one aspect, the reaction medium comprises a culture medium. In another aspect, the method comprising a prior step of sample enrichment.

In one aspect, to detect the bacteria of the *Bacillus cereus* group as distinct from other bacteria, said bacteria of the *Bacillus cereus* group being chosen from *Bacillus cereus*, *Bacillus anthracis*, *Bacillus thuringiensis*, *Bacillus mycoides*, *Bacillus pseudomycoides*, *Bacillus weihenstephanensis*, and the other bacteria being chosen from *Listeria monocytogenes*, *Listeria ivanovii*, *Staphylococcus* spp. or the other species of the genus *Bacillus* spp. such as *Bacillus subtilis*, *Bacillus amyloliquefaciens*, *Bacillus atrophaeus*, *Bacillus licheniformis*, *Bacillus sphaericus*, *Bacillus circulans*, *Bacillus lentus*, *Bacillus pumilus*, *Bacillus megaterium*.

A reaction medium for detecting bacteria of the *Bacillus cereus* group in a sample capable of containing them, said reaction medium comprising:
- at least one carboxylesterase and/or triacylglycerol-lipase substrate such as defined in one of claims 1 to 8, and
- a bacterial culture medium suitable for the bacteria to be detected, preferably a solid or semi-solid medium such as an agar medium.

In one aspect, the reaction medium further comprising at least one anti-Gram negative selective system and/or at least one antifungal agent.

DETAILED DESCRIPTION OF THE INVENTION

With regard to the problems mentioned above, the Applicant has surprisingly discovered that a carboxylesterase and/or triacylglycerol-lipase substrate of general formula (I) (cf. below) which has an aliphatic hydrocarbon chain X which comprises between 11 and 17 carbon atoms notably made it possible:
- to detect the bacteria of the *Bacillus cereus* group not only in a liquid medium but also in a semi-solid or solid medium, with a detection sensitivity and above all a "time-to-result" which is entirely satisfactory,
- to distinguish bacteria of the *Bacillus cereus* group from other *Bacillus cereus* species frequently encountered, *Bacillus subtilis* in particular, and
- to avoid having to use sophisticated apparatus; the apparatus used to implement the aforementioned carboxylesterase and/or triacylglycerol-lipase substrate of general formula (I) indeed being relatively simple.

As a consequence, an object of the invention relates to the use of at least one chromogenic and/or fluorogenic carboxylesterase and/or triacylglycerol-lipase substrate for detecting the bacteria of the *Bacillus cereus* group in a sample capable of containing them, such as a sample of agri-food origin or clinical origin, wherein said carboxylesterase and/or triacylglycerol-lipase substrate is a substrate of the general formula (I):

$$M-O-\underset{\underset{O}{\|}}{C}-X \qquad (I)$$

wherein M represents the labelling part, and
X represents an aliphatic hydrocarbon chain,
and wherein said aliphatic hydrocarbon chain comprises a number of carbon atoms between 11 and 17, for example between 12 and 16.

Of course, the invention also relates to the embodiment in which a plurality of different enzyme substrates (for example two, three, four, etc.) of general formula (I) are used in combination.

Thus the carboxylesterase and/or triacylglycerol-lipase substrates of general formula (I) as defined previously make it possible to detect the bacteria of the *Bacillus cereus* group with an optimal detection sensitivity, and above all an optimal detection specificity and a time-to-result which is entirely satisfactory, all while using a relatively simple apparatus. In particular, thanks to the optimal detection specificity obtained by the carboxylesterase and/or triacylglycerol-lipase substrates according to the invention, it now proves possible to reliably distinguish the bacteria belonging to the *Bacillus cereus* group from bacteria which are not part of this group. By way of example, the invention makes it possible to reliably distinguish the bacteria belonging to the *Bacillus cereus* group from those belonging to the *Bacillus subtilis* group.

Additionally, the Applicant has also discovered, against all expectations, that the use of at least one enzyme substrate of general formula (I) made it possible to detect the bacteria of the *Bacillus cereus* group with an optimal detection sensitivity and above all an optimal detection specificity (making it possible to reliably distinguish the bacteria belonging to the *Bacillus cereus* group from bacteria which are not part of this group) even if a lean culture medium (also commonly called a "lean medium" or "lean base") is used. "Lean culture medium" (or "lean base") is to be understood according to the meaning commonly accepted in microbiology, namely a culture medium which contains a low concentration of nutrients. A reference example of such a lean culture medium is the "R2A Agar" medium (European Pharmacopoeia; Cat. No.: 1071).

The aforementioned advantageous techniques are optimal when said aliphatic hydrocarbon chain X comprises a number of carbon atoms between 13 and 15. This therefore represents a preferred embodiment of the present invention.

According to a preferred embodiment, the detection of the bacteria of the *Bacillus cereus* group by means of said at least one carboxylesterase and/or triacylglycerol-lipase substrate of general formula (I) takes place in a solid or semi-solid medium such as an agar medium.

The above-mentioned carboxylesterase and/or triacylglycerol-lipase substrate of general formula (I) is hydrolysed by the carboxylesterase and/or triacylglycerol-lipase enzymes of the bacteria belonging to the *Bacillus cereus* group according to the following reaction:

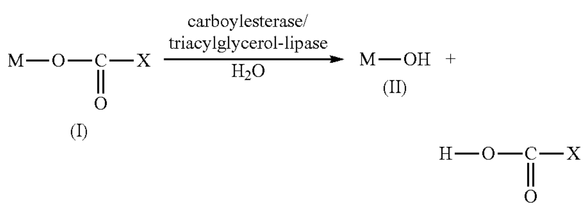

(I) (II) (III)

X preferably represents an aliphatic hydrocarbon chain, advantageously a linear and saturated aliphatic hydrocarbon chain.

According to one particularly preferred embodiment, the carboxylesterase and/or triacylglycerol-lipase substrate is chosen from 5-bromo-4-chloro-3-indoxyl-myristate, 5-bromo-4-chloro-3-indoxyl palmitate, or a combination of the two.

According to a preferred embodiment, said labelling part M is:

- a chromogenic (chromophore) labelling part selected from: indoxyls (or at least one of their derivatives, such as Aldols®, Biosynth AG, Switzerland), alizarin (also called dihydroxyanthraquinone), hydroxyquinoline, catechol, dihydroxyflavone, esculetin, nitrophenol, naphthol, or at least one of their derivatives; advantageously selected from indoxyls, alizarin, hydroxyquinoline, catechol, dihydroxyflavone, esculetin, or at least one of their derivatives; or
- a fluorogenic labelling part (fluorophore) selected from: the derivatives of fluorescein, of rhodamine, of hydroxyflavone, of ELF97.

Preferably, M represents a chromogenic labelling part (chromophore), preferably selected from indoxyls, alizarin, hydroxyquinoline, catechol, dihydroxyflavone, esculetin, or at least one of their derivatives. According to a particularly preferred embodiment, said chromogenic labelling part is based on indoxyl or one of its derivatives.

According to a particularly preferred embodiment, said aliphatic hydrocarbon chain X comprises 13 or 15 carbon atoms, preferably 13 carbon atoms.

According to a particular embodiment, said carboxylesterase and/or triacylglycerol-lipase substrate is a substrate based on indoxyl or one of its derivatives, said carboxylesterase and/or triacylglycerol-lipase substrate being used in combination with at least an agent which promotes the oxidative polymerisation of the indoxyl derivative, such as a metallic complex of the ammonium ferric citrate type.

With regard to the nomenclature of the enzyme substrates based on indoxyl (or on one of its derivatives), the roots "indoxyl" and "indolyl" should be understood as being equivalent. Thus, X-myristate may be named either "5-bromo-4-chloro-3-indoxyl-myristate" or "5-bromo-4-chloro-3-indolyl-myristate".

According to a preferred embodiment, said carboxylesterase and/or triacylglycerol-lipase substrate is contained in a reaction medium comprising at least one, preferably two and advantageously three of the following components:

- a bacterial culture medium suitable for the bacteria to be detected, preferably a solid or semi-solid medium such as an agar medium,
- an anti-Gram negative selective system,
- an antifungal agent.

Another object of the invention relates to a method for detecting bacteria of the *Bacillus cereus* group in a solid or semi-solid medium, said method comprising the following steps:

a) placing a sample capable of containing bacteria of the *Bacillus cereus* group in contact, within said solid or semi-solid medium, with a reaction medium comprising at least one carboxylesterase and/or triacylglycerol-lipase substrate such as defined previously and a Gram-negative bacteria inhibitor, said substrate being a chromogenic and/or fluorogenic substrate;

b) incubating the assembly for a time period sufficient to enable the appearance of bacterial colonies of the *Bacillus cereus* group;

c) detecting the bacteria of the *Bacillus cereus* group through observing a coloration and/or a fluorescence caused by the hydrolysis of the carboxylesterase and/or triacylglycerol-lipase substrate by said bacteria.

Of course, as the chromogenic and/or fluorogenic substrate, a substrate is used which is suitable for use in a solid or semi-solid medium, namely suitable for generating a coloration and/or a fluorescence which remain(s) localised in the zone of hydrolysis of said substrate by the enzyme activity sought. Indeed, it is important that, unlike substrates such as 4-MU-CP (4-methyl-umbelliferyl-choline phosphate), the chromogenic and/or fluorogenic substrate according to the invention generates, after hydrolysis, a chromophore and/or fluorophore which is disseminated very little—or not at all—within the solid or semi-solid medium but which remains localised on the bacterial colonies of interest (namely on the bacterial colonies formed by the bacteria of the *Bacillus cereus* group).

The reaction medium preferably comprises a culture medium.

According to a preferred embodiment, said method comprises a prior step of sample enrichment.

The invention also relates to the use of at least one carboxylesterase and/or triacylglycerol-lipase substrate as defined above to detect the bacteria of the *Bacillus cereus* group as distinct from other bacteria.

In the terms of the present invention, the bacteria of the *Bacillus cereus* group are chosen from *Bacillus cereus, Bacillus anthracis, Bacillus thuringiensis, Bacillus mycoides, Bacillus pseudomycoides, Bacillus weihenstephanensis*, and the other bacteria are chosen from *Listeria monocytogenes, Listeria ivanovii, Staphylococcus* spp. or the other species of the genus *Bacillus* spp. such as *Bacillus subtilis, Bacillus amyloliquefaciens, Bacillus atrophaeus, Bacillus licheniformis, Bacillus sphaericus, Bacillus circulans, Bacillus lentus, Bacillus pumilus, Bacillus megaterium.*

The invention also relates to a reaction medium for detecting the bacteria of the *Bacillus cereus* group in a sample capable of containing them, said reaction medium comprising:

- at least one carboxylesterase and/or triacylglycerol-lipase substrate such as defined above, and a bacterial culture medium suitable for the bacteria to be detected, preferably a solid or semi-solid medium such as an agar medium.

The reaction medium according to the invention preferably further comprises at least one anti-Gram negative selective system and/or at least one antifungal agent.

The present patent application also describes the use of at least one chromogenic and/or flurogenic carboxylesterase and/or triacylglycerol-lipase substrate for the detection of the bacteria of the Bacillus cereus group in a sample capable of containing them, such as a sample of food origin or clinical origin.

"Sample" is to be understood to be a small part or small isolated quantity of an entity for analysis. The sample can be of industrial origin, or, according to a non-exhaustive list, can be an air specimen, a water specimen, a surface specimen, a part or a manufactured product, or a food product. Amongst the samples of food origin, non-exhaustive mention can be made of a sample of dairy products (yogurts, cheeses . . . ), meat, fish, eggs, fruits, vegetables, water, beverages (milk, fruit juice, soda, etc.). These samples of food origin can also come from sauces or ready meals.

Finally, a food sample can come from an animal feed, such as notably animal meals. The sample can be of biological origin, either animal, vegetable or human. In this case it may correspond to a specimen of biological fluid (in particular whole blood, serum, plasma, urine, cerebrospinal fluid, bronchoalveolar lavage, stools, organic secretion), a tissue specimen or isolated cells. This specimen can be used as-is or, prior to the analysis, undergo preparation by enrichment, extraction, concentration or purification, in accordance with methods known to the person skilled in the art.

Microbiological monitoring corresponds to the analysis of a sample with the aim of detecting and/or enumerating microorganisms suspected/capable of being present within said sample. Reaction medium is to be understood to be a medium comprising all the elements necessary for the survival and/or for the growth of the microorganisms. This reaction medium may serve either solely as a revealing medium or as a culture and revealing medium. In the first case, the culturing of the microorganisms may be performed before seeding and, in the second case, the reaction medium also constitutes the culture medium. The reaction medium may be solid, semi-solid or liquid. A semi-solid or solid medium is understood to be a gelled medium, for example. The medium according to the invention is preferably a gelled medium. Agar is the conventional gelling agent used in microbiology for culturing microorganisms, but it is possible to use other gelling agents, such as gelrite, gelatine or agarose, for example. A number of agar media are commercially available and known to the person skilled in the art, such as Columbia agar, Trypcase-soy agar, MacConkey agar, Mueller Hinton agar, for example, or more generally those described in the Handbook of Microbiological Media (CRC Press). The reaction medium may further comprise one or more elements in combination, such as growth factors such as peptones in particular, carbohydrates, nucleotides, minerals, vitamins, sheep or horse blood, amino acids, salts, buffers, etc. This reaction medium may also comprise at least one dye or pH indicator, which may be a chromophore or a fluorophore, preferably a chromophore. As an example of a chromophore, mention can be made of neutral red, aniline blue and bromocresol blue. As a guide, mention can be made of Evans blue, neutral red, phenol red, nitroaniline, malachite green, brilliant green, etc. The medium reaction may furthermore contain an opacifying agent such as titanium dioxide, kaolin, these being given purely as a guide.

This reaction medium may take the form of a liquid, a ready-to-use gel, i.e. ready to be seeded in a tube, in a flask or on a Petri dish. With regard to the present invention, the reaction medium additionally contains a substrate making it possible to detect an enzyme or metabolic activity of the target microorganisms by means of a directly or indirectly detectable signal.

The detection of the bacteria of the Bacillus cereus group make it possible to perceive with the naked eye or with the aid of an optical device, the existence of a growth of the target bacteria (in this case belonging to the Bacillus cereus group), namely the appearance of colonies which are coloured and/or fluorescent (depending on whether the substrate used is chromogenic, fluorogenic or exhibits both characteristics at the same time), said colonies being coloured and/or fluorescent through the revelation of carboxylesterase-type and/or triacylglycerol-lipase-type enzyme activity of the bacteria of the Bacillus cereus group on said carboxylesterase and/or triacylglycerol-lipase substrate.

As indicated previously, the detection of the fluorescence emitted after cleavage of the fluorogenic enzyme substrates makes it necessary to use an optical device, whereas the cleavage of the chromogenic enzyme substrates may be observed with the naked eye or, if needed, with the aid of an optical device. Advantageously, the detection of the bacteria of the Bacillus cereus group also makes it possible to identify and/or enumerate them.

The enumeration of the bacteria of the Bacillus cereus group, for its part, consists in quantifying the number of colonies of bacteria of the Bacillus cereus group which has grown on the culture medium by employing microbiology techniques well known to the person skilled in the art.

Employing a chromogenic and/or fluorogenic, preferably chromogenic, carboxylesterase and/or triacylglycerol-lipase substrate makes it possible to obtain highly satisfactory detection sensitivity while conferring very good specificity: the majority of the Gram-positive bacteria detected are bacteria of the Bacillus cereus group. The other Gram-positive and Gram-negative bacteria are not coloured and/or fluorescent.

Furthermore, such a carboxylesterase and/or triacylglycerol-lipase substrate exerts very little inhibition—or even none at all—on the growth of the bacteria of the Bacillus cereus group on the culture media, which represents a not insignificant advantage.

Chromogenic and/or fluorogenic substrate is to be understood to be a substrate which makes it possible to detect an enzyme or metabolic activity of the target/sought microorganisms by means of a directly or indirectly detectable signal. For direct detection, this substrate can be bound to a part acting as a fluorogenic or chromogenic label (Orenga et al., 2009; J. Microbiol. Methods; 79(2):139-55)), preferably chromogenic in the terms of the present invention. For indirect detection, the reaction medium according to the invention can also contain a pH indicator which is sensitive to the pH variation induced by the consumption of the substrate and which reveals the metabolism of the target microorganisms. Said pH indicator can be a chromophore or a fluorophore. As examples of chromophores, mention can be made of bromocresol purple, bromothymol blue, neutral red, aniline blue and bromocresol blue.

As indicated previously, according to a particularly advantageous embodiment, it is important that the chromogenic and/or fluorogenic substrate according to the invention is suitable for use in a solid or semi-solid medium, namely suitable for generating a coloration and/or a fluorescence which remain(s) localised at the zone of hydrolysis of said substrate by the enzyme activity sought. Indeed, it is important that, unlike substrates such as 4 MU-CP (4-methyl-umbelliferyl-choline phosphate), the chromogenic and/or fluorogenic substrate according to the invention is disseminated very little—or not at all—within the solid or semi-solid medium but remains localised on the bacterial colonies of interest (namely on the bacterial colonies formed by the bacteria of the *Bacillus cereus* group).

"Carboxylesterase and/or triacylglycerol-lipase substrate" should be understood to be an enzyme substrate which, after reaction with a carboxylesterase-type enzyme (enzyme classification: E.C. 3.1.1.1) and/or triacylglycerol-lipase-type enzyme (enzyme classification E.C. 3.1.1.3), is capable of giving rise to a coloured and/or fluorescent reaction, depending on whether a chromogenic and/or fluorogenic substrate is used.

The chromogenic and/or fluorogenic carboxylesterase and/or triacylglycerol-lipase substrates used according to the present invention are preferably synthetic substrates made up of two parts, a first part which is specific to the enzyme activity to be detected, namely a carboxylesterase-type and/or triacylglycerol-lipase-type enzyme activity, and a second part which acts as a label, hereafter called the "labelling part". The labelling part is chromogenic and/or fluorogenic (chromophore and/or fluorophore) when it is no longer associated with the first part, namely after cleavage by the carboxylesterase and/or triacylglycerol-lipase enzyme (within the framework of a hydrolysis-type reaction) and separation of said first and second parts.

The chromogenic enzyme substrates (comprising at least one chromophore) usable in the terms of the present invention can be of different kinds.

Firstly, mention should be made of chromophores of the indoxyl type and derivatives thereof which, in the presence of oxygen, produce a precipitate varying from blue to pink. The addition of an agent which promotes oxidative polymerisation of the indoxyl derivative, such as a metal complex of the ammonium ferric citrate type in the culture medium may prove to be advantageous. The carboxylesterase and/or triacylglycerol-lipase substrates based on indoxyl and its derivatives are particularly preferred in the terms of the present invention due to their relatively easy implementation and their good sensitivity for detecting the target bacteria (notably for the purpose of identifying and/or enumerating the latter), in this case for detecting the bacteria of the *B. cereus* group. The indoxyl-based substrates (by way of example, 5-bromo-4-chloro-3-indoxyl-beta-D-glucopyranoside or X-beta-glucoside can be cited) are generally well known to the person skilled in the art and are widely used in the chromogenic media on the market. Their applications essentially relate to the enzyme activities of the osidase, lipase and phosphatase types (phosphatase being an esterase activity of phosphoric acid). Well suited to a use on a solid or semi-solid support (filter, agar, electrophoresis gel, etc.), they are less suited to use in liquid medium (formation of a precipitate).

The Aldol®-type chromophores (Biosynth® AG) also represent chromophores of interest in terms of the present invention, insofar as the appearance of a coloured precipitate does not require any addition (oxygen, metal salts, etc.). The use of Aldol®-based enzyme substrates may therefore prove to be particularly advantageous within the framework of pour plate seeding of bacteria. These Aldol® chromophores are particular derivatives of indoxyl (1H-indolyl-3-yl), namely indoxyls joined onto the cyclic amine (N-arylated), such as disclosed in the PCT patent application published under the reference WO 2010/128120 (in the name of Biosynth® AG [CH]). Such enzyme substrates can be obtained from Biosynth® AG.

Secondly, there are chromophores such as hydroxyquinoline, dihydroxyanthraquinone, catechol, dihydroxyflavone or esculetin and their derivatives which, in the presence of iron salts, produce a coloured precipitate. Here too, their applications primarily relate to enzyme activities of the osidase, esterase and phosphatase type.

Thirdly, there are naphthol-based enzyme substrates. In this case, the enzyme-substrate reaction is performed in two steps, the naphthol released as a result of the expression of enzyme activity undergoes "azo-coupling" in the presence of a diazonium salt which is added at the moment of revelation, leading to the formation of an insoluble coloured compound. They also make it possible to detect osidase and esterase activities via naphthol. The "azo-coupling" reaction is performed in a medium which is often chemically aggressive, toxic to the bacteria and which makes the sample unusable for other analyses.

According to a preferred embodiment of the present invention, the labelling part of the enzyme substrate according to the invention is a labelling part which is preferably chosen from indoxyls and their derivatives (3-Indoxyl, 5-Bromo-3-indoxyl, 5-Iodo-3-indoxyl, 4-Chloro-3-indoxyl, 5-Bromo-4-chloro-3-indoxyl, 5-Bromo-6-chloro-3-indoxyl, 6-Bromo-3-indoxyl, 6-Chloro-3-indoxyl, 6-Fluoro-3-indoxyl, 5-Bromo-4-chloro-3-indoxyl-N-methyl, N-Methyl-3-indoxyl, Aldol® . . . ); alizarin; hydroxyquinoline; catechol; dihydroxyflavone, hydroxyflavone, naphthol, ELF97, esculetin or one of the derivatives. Preferably, said labelling part is a chromogenic labelling part, advantageously based on indoxyl (indolyl) or one of its derivatives.

Preferably, the chromogenic and/or fluorogenic, advantageously chromogenic, carboxylesterase and/or triacylglycerol-lipase substrate according to the present invention is selected from: 3-Indoxyl-myristate, 5-Bromo-3-indoxyl-myristate, 5-Iodo-3-indoxyl-myristate, 4-Chloro-3-indoxyl-myristate, 5-Bromo-4-chloro-3-indoxyl-myristate, 5-Bromo-6-chloro-3-indoxyl-myristate, 6-Bromo-3-indoxyl-myristate, 6-Chloro-3-indoxyl-myristate, 6-Fluoro-3-indoxyl-myristate, 5-Bromo-4-chloro-3-indoxyl-N-methyl-myristate, N-Methyl-3-indoxyl-myristate, Aldol®-myristate; 3-Indoxyl-palmitate, 5-Bromo-3-indoxyl-palmitate, 5-Iodo-3-indoxyl-palmitate, 4-Chloro-3-indoxyl-palmitate, 5-Bromo-4-chloro-3-indoxyl-palmitate, 5-Bromo-6-chloro-3-indoxyl-palmitate, 6-Bromo-3-indoxyl-palmitate, 6-Chloro-3-indoxyl-palmitate, 6-Fluoro-3-indoxyl-palmitate, 5-Bromo-4-chloro-3-indoxyl-N-methyl-palmitate, N-Methyl-3-indoxyl-palmitate, Aldol®-palmitate, Alizarin-myristate, alizarin-palmitate, 3,4-cyclohexenoesculetin-myristate (CHE-myristate), 3,4-cyclohexenoesculetin- -palmitate (CHE-palmitate), catechol-myristate, catechol-palmitate, dihydroxyflavone-myristate, dihydroxyflavone-palmitate, hydroxyquinoline-myristate and hydroxyquinoline-palmitate. Advantageously, said substrate is 5-bromo-4-chloro-3-indoxyl-myristate (X-C14) or 5-bromo-4-chloro-3-indoxyl-palmitate (X-C16). According to a particular embodiment, a combination of 5-bromo-4-chloro-3-indoxyl-myristate (X-C14) and 5-bromo-4-chloro-3-indoxyl-palmitate (X-C16) can be used for the purposes of the present invention.

According to a particular embodiment, said substrate is a carboxylesterase and triacylglycerol-lipase substrate.

As indicated above, the carboxylesterase and/or triacylglycerol-lipase substrate is preferably a chromogenic substrate which can be cleaved by the carboxylesterase and/or triacylglycerol-lipase activity of bacteria of the Bacillus cereus group. Thus, this chromogenic substrate is, preferably, a substrate made up of a target part and a labelling part. The hydrolysis of the substrate by the carboxylesterase and/or triacylglycerol-lipase enzyme of the bacteria of the Bacillus cereus group induces the separation (cleavage) of the target part and the labelling part, said target part characterising the carboxylesterase and/or triacylglycerol-lipase enzyme activity and said labelling part being a molecule which makes it possible to reveal the hydrolysis reaction via the appearance of coloration at the hydrolysis site: on the colonies.

The person skilled in the art may also use a bi-plate, which makes it possible to easily compare two media, comprising different substrates or different selective mixtures, onto which the same biological sample will have been deposited. The reaction medium may comprise one or more selective agents which make it possible to inhibit the growth of the Gram-negative germs, of yeasts and moulds and of Gram-positive bacteria apart from the bacteria of interest—constituted here by the bacteria of the B. cereus group.

"Selective agent" is to be understood to be any compound capable of preventing or slowing the growth of a microorganism other than the target microorganism. By way of example, antibiotics, antifungals, or lithium chloride may be used. Without being limiting, a concentration of between 0.01 mg/l and 5 g/l of selective agent(s) is particularly suitable for the present invention.

Concerning the anti-Gram negative (anti-Gram–), anti-Gram positive (anti-Gram+) and/or antifungal selective systems, these latter are well-known to the person skilled in the art. By way of example, in the anti-Gram negative selective system used for the purposes of the present invention, one or more selective agent(s) selected from nalidixic acid, aztreonam, polymyxin B, colistin is/are used at concentrations known to the person skilled in the art to obtain the desired effect, namely the elimination of the Gram-negative bacteria.

An antifungal (or "antifungal agent") is understood to be any compound capable of preventing or slowing the growth of a yeast or a mould. As a guide, it is possible to mention in particular amphotericin B, fluconazole, itraconazole, voriconazole, cycloheximide and 5-fluorocytosine. Preferably, at least one antifungal agent is used at concentrations known to the person skilled in the art to obtain the aforementioned effect.

An "antibiotic" is understood to be any compound capable of preventing or slowing the growth of a bacterium. In particular, antibiotics belong to the beta-lactam, glycopeptide, aminoglycoside, polypeptide, sulfonamide and quinolone groups. As a guide, it is in particular possible to mention the antibiotics cefotaxime, cefsulodin, ceftazidime, cefoxitin, ceftriaxone, cefpodoxime, aztreonam, vancomycin, gentamicin, Trimethoprim, nisin, tobramycin, moxalactam, fosfomycin, D-cycloserine, Polymyxin, Colistin, and quinolones such as nalidixic acid.

"Incubate" is to be understood to mean raising to and holding at, for between 1 and 48 hours, preferably between 4 and 24 hours, more preferably between 16 and 24 hours, an appropriate temperature, generally of between 20 and 50° C., preferably between 30 and 40° C.

In the terms of the present invention, the definition of "detection sensitivity" is identical to the one commonly recognised in the state of the art, namely the ability to give a positive result (appearance of a coloured and/or fluorescent reaction) when the target bacterial strain—in this case belonging to the Bacillus cereus group—is present in the sample.

The same applies to detection specificity, whose definition conforms to that recognised in the state of the art, namely as the ability to give a negative result (absence of a coloured and/or fluorescent reaction) when a strain other than the target bacterial strain—in this case belonging to the Bacillus cereus group—is present in the sample tested.

The chromogenic and/or fluorogenic carboxylesterase and/or triacylglycerol-lipase substrate is used at a concentration sufficient to make it possible to detect the appearance of a coloured and/or fluorescent reaction after cleavage by the bacteria of the Bacillus cereus group. This concentration is known to the person skilled in the art or at the very least is easy for him/her to determine. As an illustration, the concentration of chromogenic and/or fluorogenic carboxylesterase and/or fluorogenic substrate is generally between 1 mg/L and 10 g/L, preferably between 5 mg/L and 6 g/L, preferably between 25 mg/L and 2 g/L and advantageously between 25 mg/L and 500 mg/L.

Example 1

1.1 Operating Procedure

For the purposes of this example, a lean base is used, the composition of which is detailed in table 1 presented below:

TABLE 1 composition of the lean base

| Compounds | Concentration in g/L |
| --- | --- |
| Glucose | 0.25 |
| Agar | 13 |
| Yeast extract | 2 |
| Sodium pyruvate | 0.25 |
| NaCl | 5 |
| Buffer | 0.16 |

The various compounds of this lean base are weighed one by one. The whole is taken up in a necessary volume of osmosis-treated water. The media are melted at 100° C. and sterilised by autoclaving (121° C. cycle for 15 minutes).

After the media have returned to 55° C., the 5-bromo-4-chloro-3-indoxyl-myristate ($X-C_{14}$) and 5-bromo-4-chloro-3-indoxyl-palmitate ($X-C_{16}$) enzyme substrates—both carboxylesterase and triacylglycerol-lipase substrates—are added. To do so, stock solutions are prepared at 75 g/L in a DMSO-type organic solvent. A volume of Tween 20 is added to the stock solution volume necessary to obtain a final concentration of enzyme substrates of 150 mg/L.

The media are divided into sterile Petri dishes before being seeded.

Table 2 below summarises the enzyme substrate composition of the media tested:

TABLE 2 composition of the tested media

| | Lean base | | |
|---|---|---|---|
| Concentration in mg/L | Control medium (T) | Medium 1 | Medium 2 |
| X-C14 | 0 | 150 | 0 |
| X-C16 | 0 | 0 | 150 |

39 strains of *Bacillus* spp were tested on each of the aforementioned three media. To do so, each of the media was seeded with the aid of a 10 µL sterile loop from bacterial suspensions calibrated to 0.5 McF with the aid of a densitometer; suspensions produced in 0.85% saline (bioMérieux ref. 20040).

The media were then incubated for 48 hours at 37° C. Readings were carried out after 24 and 48 hours of incubation. The growth (number of dials and size of the isolated colonies) as well as the coloration intensities obtained (expression of the target enzyme activity) were noted for each of these two reading times. The table of results below only records coloration intensities. However, NG ("no growth") is noted when growth of the strain is inhibited. The intensity is read on a scale ranging from 0 to 4, with 0 for no coloration and 4 for a maximum coloration intensity.

1.2 Results

The results at 24 and 48 hours of incubation are respectively presented in tables 3 and 4 below.

TABLE 3 results after 24 hours of incubation

| Strains | API/QI No. | Medium T | Medium 1 | Medium 2 |
|---|---|---|---|---|
| B. cereus | 02 04 010 | 0 | 1.5 | 1.5 |
| B. cereus | 02 04 001 | 0 | 1.5 | 1.5 |
| B. cereus/thuringiensis | 611 | 0 | 2.5 | 2.5 |
| B. cereus/thuringiensis | 691 | 0 | 2 | 2 |
| B. cereus | 01 06 003 | 0 | 0 | 0 |
| B. thuringiensis | 02 04 018 | 0 | 2.5 | 2.5 |
| B. thuringiensis | 02 04 012 | 0 | 2 | 1.5 |
| B. mycoides | 02 04 030 | 0 | 0 | 0 |
| Bacillus weihenstephanensis | 09 06 189 | 0 | 1 | 0.5 |
| B. cereus/thuringiensis | 07 06 021 | 0 | 0.5 | 0.5 |
| B. cereus | 11 05 179 | 0 | 0 | 0 |
| B. mycoides | 94 05 092 | 0 | 1 | 0.1 |
| B. pseudomycoides | 09 02 022 | 0 | 1.5 | 1.5 |
| B. cereus | 78 02 085 | 0 | 0.5 | 0 |
| B. subtilis | 632 | 0 | 0 | 0 |
| B. licheniformis | 574 | 0 | 0 | 0 |
| B. subtilis ssp spizizenii | 08 01 024 | 0 | 0 | 0 |
| B. circulans | 02 04 033 | 0 | 0 | 0 |
| B. circulans | 628 | 0 | 0 | 0 |
| B. badius | 02 04 032 | 0 | 0 | 0 |
| B. atrophaeus | 90 06 035 | 0 | 0 | 0 |
| B. amyloliquefaciens | 01 02 055 | 0 | 0 | 0 |
| B. licheniformis | 514 | 0 | 0 | 0 |
| B. coagulans | 02 04 050 | 0 | 0 | 0 |
| B. pumilus | 22 | 0 | 0 | 0 |
| B. lentus | 630 | 0 | 0 | 0 |
| B. firmus | 93 08 075 | 0 | 0 | 0 |
| B. amyloliquefaciens | 90 08 024 | 0 | 1 | 0 |
| B. lentus | 93 08 070 | 0 | 0 | 0 |
| B. pumilus | 02 04 036 | 0 | 1.5 | 1.5 |
| B. clausii | 98 08 107 | 0 | 0 | 0 |
| B. vietnamensis | 05 05 001 | NG | NG | NG |
| B. subtilis | 09 11 166 | 0 | 1.5 | 1 |
| B. megaterium | 92 06 025 | 0 | 0 | 0 |
| B. subtilis | 91 08 005 | 0 | 1.5 | 1 |
| B. amyloliquefaciens | 90 08 027 | 0 | 1.5 | 0 |
| B. licheniformis | 88 07 023 | 0 | 0 | 0 |
| B. megaterium | 87 05 008 | 0 | 0 | 0 |
| B. firmus | 09 07 061 | 0 | 0 | 0 |
| Detection sensitivity B. cereus group (14) in (%) | | N/A | 78.5 | 71.5 |
| Detection specificity (25) in % | | N/A | 80 | 88 |

Key:
NG = no growth
0 = growth, no coloration
1 = low coloration intensity
2 = intermediate coloration intensity
3 = high coloration intensity
4 = maximum coloration intensity

TABLE 4 results after 48 hours of incubation

| Strains | API/QI No. | Medium T | Medium 1 | Medium 2 |
|---|---|---|---|---|
| B. cereus | 02 04 010 | 0 | 2 | 2 |
| B. cereus | 02 04 001 | 0 | 2.5 | 2.5 |
| B. cereus/thuringiensis | 611 | 0 | 2.5 | 2.5 |
| B. cereus/thuringiensis | 691 | 0 | 2 | 2 |
| B. cereus | 01 06 003 | 0 | 2.5 | 2.5 |
| B. thuringiensis | 02 04 018 | 0 | 2.5 | 2.5 |
| B. thuringiensis | 02 04 012 | 0 | 2 | 2 |
| B. mycoides | 02 04 030 | 0 | 2 | 2 |
| Bacillus weihenstephanensis | 09 06 189 | 0 | 2.5 | 2.5 |
| B. cereus/thuringiensis | 07 06 021 | 0 | 1.5 | 1.5 |
| B. cereus | 11 05 179 | 0 | 1 | 0.5 |
| B. mycoides | 94 05 092 | 0 | 2 | 1.5 |
| B. pseudomycoides | 09 02 022 | 0 | 2 | 2 |
| B. cereus | 78 02 085 | 0 | 1.5 | 1 |
| B. subtilis | 632 | 0 | 0 | 0 |
| B. licheniformis | 574 | 0 | 0 | 0 |
| B. subtilis ssp spizizenii | 08 01 024 | 0 | 0 | 0 |
| B. circulans | 02 04 033 | 0 | 0 | 0 |
| B. circulans | 628 | 0 | 0 | 0 |
| B. badius | 02 04 032 | 0 | 0 | 0 |
| B. atrophaeus | 90 06 035 | 0 | 0 | 0 |
| B. amyloliquefaciens | 01 02 055 | 0 | 0 | 0 |
| B. licheniformis | 514 | 0 | 0 | 0 |
| B. coagulans | 02 04 050 | 0 | 0 | 0 |
| B. pumilus | 22 | 0 | 0 | 0 |
| B. lentus | 630 | 0 | 0 | 0 |
| B. firmus | 93 08 075 | 0 | 0 | 0 |
| B. amyloliquefaciens | 90 08 024 | 0 | 1.5 | 0.5 |
| B. lentus | 93 08 070 | 0 | 0 | 0 |
| B. pumilus | 02 04 036 | 0 | 2 | 1.5 |
| B. clausii | 98 08 107 | 0 | 2 | 1.5 |
| B. vietnamensis | 05 05 001 | 0 | 0 | 0 |
| B. subtilis | 09 11 166 | 0 | 2 | 1.5 |
| B. megaterium | 92 06 025 | 0 | 0 | 0 |
| B. subtilis | 91 08 005 | 0 | 2 | 1.5 |
| B. amyloliquefaciens | 90 08 027 | 0 | 1.5 | 0 |
| B. licheniformis | 88 07 023 | 0 | 0 | 0 |
| B. megaterium | 87 05 008 | 0 | 0 | 0 |
| B. firmus | 09 07 061 | 0 | 0.5 | 0 |
| Detection sensitivity B. cereus group (14) in (%) | | N/A | 100 | 100 |
| Detection specificity (25) in % | | N/A | 72 | 80 |

Key:
NG = no growth
0 = growth, no coloration
1 = low coloration intensity
2 = intermediate coloration intensity
3 = high coloration intensity
4 = maximum coloration intensity For the purposes of determining the detection sensitivity and specificity, a bacterial strain is deemed to be "detected"

when the intensity of the coloration revealed is greater than or equal to 0.5 when applying the aforementioned scale for determining the coloration intensity.

The detection sensitivity (in %) is defined as follows:

(number of bacteria of the *Bacillus cereus* group "detected"/total number of bacteria of the *Bacillus cereus* group tested)×100.

enzyme substrate concentrations of 0.15 g/L, starting from 50 g/L stock solutions.

The following surfactants were used:
Tween 20 6 g/L, and
Triton X305: 3 and 6 g/L 2.2 Results The results thus obtained are presented below, in Table 5.

TABLE 5

| | Results | | | | |
|---|---|---|---|---|---|
| Media | Fertility of strains of the *B. cereus* group (17 strains) | Sensitivity of *B. cereus* group in (%) | Fertility of strains of the *B. subtilis* group (5 strains) | Fertility of other *Bacillus* sp (9 strains) | Specificity (in %) (14 strains) |
| Lean base (growth control) | 100% | N/A | N/A | 78% | N/A |
| Lean base + MPLD + TWEEN 20 | 94% | | | 78% | |
| Lean base + MPLD + Triton X305 3 g/L | 82% | | | 78% | |
| Lean base + MPLD + Triton X305 6 g/L | 82% | | | 78% | |
| X-C14/Tween 20 6 g/L | 94% | 88% | 100% | 78% | 93% |
| X-C14/Triton X305 3 g/L | 88% | 100% | 100% | 89% | 86% |
| X-C14/Triton X305 6 g/L | 82% | 100% | 100% | 78% | 93% |
| X-C16/Triton X305 3 g/L | 88% | 100% | 100% | 89% | 93% |
| X-C16/Triton X305 6 g/L | 94% | 100% | 100% | 56% | 93% |

MPLD: 1-methyl-2-pyrrolidinone

The detection specificity (in %) is defined as follows:

((total number of non-*Bacillus cereus* bacteria−number of non-*Bacillus cereus* bacteria "detected")/total number of non-*Bacillus cereus* bacteria tested)×100.

"Non-*Bacillus cereus* bacteria" is understood to mean bacteria which do not belong to the *Bacillus cereus* group.

1.3 Conclusion

The use of the carboxylesterase and triacylglycerol-lipase substrates X-C14 and X-C16 (under the implemented conditions) makes it possible to detect the strains of the *Bacillus cereus* group with a high detection sensitivity (and also high detection intensities)—especially after 48 h of incubation—while enabling a highly satisfactory detection specificity. This is all the more surprising since this detection occurs in a "lean base", a priori less favourable for growth of the bacteria of the *Bacillus cereus* group.

It emerges clearly from this experiment that it is possible to distinguish the *Bacillus cereus* group from the other *Bacillus* species frequently encountered, in particular *Bacillus subtilis*, by means of the substrates X-$C_{14}$ and X-$C_{16}$.

Example 2

2.1 Operating Procedure

In the autoclaved lean base in example 1 (the composition of which is presented in the aforementioned table 1), brought back to 55° C., different chromogenic or fluorogenic substrates were tested with different surface active agents (surfactants). 31 bacterial strains (of the genus *Bacillus*) were spot-test seeded, at 1 µL apiece from 0.5 MacFarland suspensions calibrated with the aid of a densitometer. The dishes were then incubated aerobically, for 24 hours, at 30-35° C.

The chromogenic enzyme substrates 5-bromo-4-chloro-3-indoxyl-myristate (X-$C_{14}$) and 5-bromo-4-chloro-3-indoxyl-palmitate (X-$C_{16}$) were used so as to obtain final Table 5: Results The use of an indoxyl-based substrate containing 14 or 16 carbon atoms makes it possible to obtain an optimal distinction between the bacteria of the *B. cereus* group and those which do not belong to it, in particular between the two main groups which are *B. cereus* and *B. subtilis*.

2.3 Conclusion:

A distinction is possible between the bacteria of the *B. cereus* group and those which do not belong to this—in particular between the 2 main groups which are *B. cereus* and *B. subtilis*—with the fluorogenic or chromogenic enzyme substrates used. This distinction proves to be optimal when the enzyme substrate used is an indoxyl-based substrate containing 14 or 16 carbon atoms.

Example 3

3.1 Operating Procedure

In the autoclaved lean base in example 1 (the composition of which is presented in the aforementioned table 1), brought back to a temperature of 55° C., substrates of esterases (carboxylesterase) based on alizarin with carbon chains ranging from 12 to 16 carbon atoms were tested. The stock solutions of the substrates were produced at concentrations of 12.5, 25 and 50 g/L solubilised in DMSO-type organic solvent, mixed with a Tween-type surfactant and added to the media such that the end concentration of substrates was respectively 50, 100 and 200 mg/L, always with same quantity of solvent and surfactant added to the final media.

The bacterial strains were spot-test seeded, at 1 µL apiece from 0.5 MacFarland suspensions calibrated with the aid of a densitometer. The dishes were then incubated aerobically, for 24 hours, at 30-35° C.

3.2 Results

The results thus obtained are presented below, in table 6.

TABLE 6

| Results | | | | | |
|---|---|---|---|---|---|
| Media | Fertility of *B. cereus* group (17 strains) | Sensitivity of *B. cereus* group in (%) | Fertility of *B. subtilis* group (5 strains) | Fertility of other *Bacillus* sp (9 strains) | Specificity (in %) (14 strains) |
| Lean base growth control | 100% | N/A | N/A | 78% | N/A |
| Lean base + MPLD + Tween 20 | 94% | | | 78% | |
| Alizarin-C12/Tween 20 6 g/L | 88% | 88% | 100% | 67% | 64% |
| Alizarin-C14/Tween 20 6 g/L | 88% | 94% | 100% | 78% | 79% |
| Alizarin-C16/Tween 20 6 g/L | 94% | 100% | 100% | 78% | 64% |

For the purposes of determining the detection sensitivity and specificity, a bacterial strain is deemed to be "detected" when the coloration intensity revealed is greater than or equal to 0.5 when applying the scale for determining the coloration intensity which is presented in point 1.2 above.

The detection sensitivity and specificity are also determined as detailed in point 1.2 above.

3.3 Conclusion

The alizarin-based substrates make it possible to distinguish the bacteria of the *B. cereus* group from bacteria which do not belong to this group with very good sensitivity and satisfactory specificity (greater than 60%), the greatest specificity being achieved with the "Alizarin-C14" enzyme substrate, containing 14 carbon atoms.

The invention claimed is:

1. A method for selectively detecting bacteria of the *Bacillus cereus* group, among bacteria of the genus *Bacillus*, in a solid or semi-solid reaction medium, the method comprising:

a) placing a sample in contact with the reaction medium, the reaction medium comprising at least one carboxylesterase or triacylglycerol-lipase substrate, a Gram-negative bacteria inhibitor, an antifungal agent and a selective Gram-positive bacteria inhibitor;

b) incubating the assembly of step (a) for a time period until bacterial colonies appear; and c) detecting the bacteria of the *Bacillus cereus* group through observing a coloration or a fluorescence caused by the hydrolysis of the carboxylesterase or the triacylglycerol-lipase substrate by said bacteria, wherein the carboxylesterase or the triacylglycerol-lipase substrate is a substrate of the general formula (I):

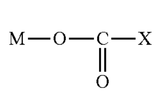

(I)

wherein M is a labelling part; and

X is an aliphatic hydrocarbon chain, wherein the aliphatic hydrocarbon chain comprises a number of carbon atoms between 11 and 17, and wherein the bacteria of the *Bacillus cereus* group are selected from the group consisting of *Bacillus cereus, Bacillus anthracis, Bacillus thuringiensis, Bacillus mycoides, Bacillus pseudomycoides*, and *Bacillus weihenstephanensis*.

2. The method according to claim 1, wherein the sample is of agri-food or clinical origin.

3. The method according to claim 1, wherein X is a linear aliphatic hydrocarbon chain.

4. The method according to claim 1, wherein X is a linear and saturated aliphatic hydrocarbon chain.

5. The method according to claim 1, wherein the labelling part M is:

a) a chromogenic labelling part selected from the group consisting of indoxyls, alizarin, hydroxyquinoline, catechol, dihydroxyflavone, esculetin, nitrophenol, naphthol, and derivatives thereof; or b) a fluorogenic labelling part selected from the group consisting of derivatives of fluorescein, rhodamine, hydroxyflavone, and ELF97.

6. The method according to claim 5, wherein the chromogenic labelling part M is selected from the group consisting of indoxyls, alizarin, hydroxyquinoline, catechol, dihydroxyflavone, esculetin, and derivatives thereof.

7. The method according to claim 1, wherein the aliphatic hydrocarbon chain X comprises a number of carbon atoms between 13 and 15.

8. The method according to claim 7, wherein the aliphatic hydrocarbon chain X comprises 13 carbon atoms.

9. The method according to claim 1, wherein the carboxylesterase or the triacylglycerol-lipase substrate is a substrate based on indoxyl or one of its derivatives, the method further comprising combining the carboxylesterase or the triacylglycerol-lipase substrate with at least one agent that promotes the oxidative polymerisation of the indoxyl derivative.

10. The method according to claim 9, wherein the agent that promotes the oxidative polymerisation of the indoxyl derivative comprises an ammonium ferric citrate metal complex.

11. The method according to claim 1, wherein the solid or semi-solid reaction medium is an agar medium.

12. The method according to claim 1, wherein the reaction medium comprises a bacterial culture medium suitable for the bacteria to be detected.

13. The method according to claim 1, further comprising a step of enrichment of the sample prior to step a).

14. The method according to claim 1, wherein the sample further contains other species of the genus *Bacillus*.

15. The method according to claim 14, wherein the other species of the genus *Bacillus* is/are selected from one or more of *Bacillus subtilis, Bacillus amyloliquefaciens, Bacillus atrophaeus, Bacillus licheniformis, Bacillus sphaericus, Bacillus circulans, Bacillus lentus, Bacillus pumilus*, and *Bacillus megaterium*.

16. The method according to claim 1, wherein the Gram-negative bacteria inhibitor is selected from at least one of nalidixic acid, aztreonam, polymyxin B, and colistin.

* * * * *